United States Patent
Narasimhamoorthy et al.

(10) Patent No.: US 9,867,341 B2
(45) Date of Patent: Jan. 16, 2018

(54) MARIGOLD INBRED LINE DENOMINATED KI4537

(71) Applicant: Kemin Industries, Inc., Des Moines, IA (US)

(72) Inventors: Brindha Narasimhamoorthy, West Des Moines, IA (US); Justin Cox, Amarillo, TX (US); Liuqing Zhao, Zhuhai (CN); Xin Liu, Zhuhai (CN); John A. Greaves, Ankeny, IA (US)

(73) Assignee: KEMIN INDUSTRIES, INC., Des Moines, IA (US)

( * ) Notice: Subject to any disclaimer, the term of this patent is extended or adjusted under 35 U.S.C. 154(b) by 118 days.

(21) Appl. No.: 14/969,751

(22) Filed: Dec. 15, 2015

(65) Prior Publication Data

US 2016/0205881 A1 Jul. 21, 2016

Related U.S. Application Data

(60) Provisional application No. 62/092,572, filed on Dec. 16, 2014.

(51) Int. Cl.
*A01H 5/02* (2006.01)

(52) U.S. Cl.
CPC .................................. *A01H 5/025* (2013.01)

(58) Field of Classification Search
None
See application file for complete search history.

(56) References Cited

U.S. PATENT DOCUMENTS

| | | | |
|---|---|---|---|
| 6,784,351 B2 | 8/2004 | Hauptmann et al. | |
| 6,894,208 B2 | 5/2005 | Winner | |
| 7,033,622 B2 | 4/2006 | Hauptmann et al. | |
| 7,575,766 B2 * | 8/2009 | Hauptmann | A01H 1/06 424/725 |
| 2002/0120965 A1 | 8/2002 | Winner | |
| 2004/0010826 A1 | 1/2004 | Hauptmann et al. | |

OTHER PUBLICATIONS

Miki et al., "Procedures for Introducing Foreign DNA into Plants", "Methods in Plant Molecular Biology and Biotechnology", , pp. 67-88, Publisher: CRC Press, Inc., Published in: Boca Raton.
International Searching Authority, "Search Report and Written Opinion," issued in connection with International Patent Application No. PCT/US2015/65814, dated Feb. 19, 2016, 6 pages.

* cited by examiner

*Primary Examiner* — David H Kruse
(74) *Attorney, Agent, or Firm* — Nyemaster Goode P.C.

(57) ABSTRACT

A new and distinct inbred plant of *Tagetes erecta* named KI4537 and characterized by elevated levels of lutein and fertile male flowers.

21 Claims, 2 Drawing Sheets

MARIGOLD INBRED LINE DENOMINATED KI4537

This application claims the benefit of U.S. Patent Application Ser. No. 62/092,572, filed Dec. 16, 2014, and incorporated herein in its entirety by this reference.

FILED OF THE INVENTION

The present invention relates generally to a homozygous inbred line of marigold (*Tagetes erecta*) and, more specifically, to marigold line denominated KI4537 that produces a high amount of xanthophylls, and specifically lutein, and which has male fertile flowers.

BACKGROUND OF THE INVENTION

Xanthophylls are yellow pigments that form one of two major divisions of the carotenoid group. Their molecular structure is similar to carotenes, which form the other major carotenoid group division, but xanthophylls contain oxygen atoms, while carotenes are purely hydrocarbons with no oxygen. Xanthophylls contain their oxygen either as hydroxyl groups and/or as pairs of hydrogen atoms that are substituted by oxygen atoms acting as a bridge (epoxide).

Like other carotenoids, xanthophylls are found in highest quantity in the leaves and/or flowers of most green plants, where they act to modulate light energy. The xanthophylls found in the bodies of animals, and in dietary animal products, are ultimately derived from plant sources in the diet. For example, the yellow color of chicken egg yolks, fat, and skin comes from ingested xanthophylls (primarily lutein, which is often added to chicken feed for this purpose).

The yellow color of the human macula lutea in the retina of the eye comes from the lutein and zeaxanthin it contains, both xanthophylls again requiring a source in the human diet to be present in the eye. These function in eye protection from ionizing blue light, which they absorb.

The group of xanthophylls includes (among many other compounds) lutein, zeaxanthin, neoxanthin, violaxanthin, and α- and β-cryptoxanthin.

There is an interest in developing products that have high levels of xanthophylls. For example, xanthophylls are known to have antioxidant properties and have been shown to prevent age-related macular degeneration (AMD).

Marigold flowers are the most commercially significant source of xanthophylls. Most marigold plants used for the production of xanthopyulls are grown from hybrid seed produced by the crossing of a male line and a female line. Accordingly, male and/or female lines of marigold having high levels of xanthophylls can be used to create hybrid seed that can be used to grow hybrid marigold plants with elevated levels of xanthophylls, and thereby improve the economy of producing xanthopyulls for the commercial marketplace, particularly if the hybrid plants have a large biomass of flowers that can be reliably harvested.

SUMMARY OF THE INVENTION

The invention consists of a plant of *Tagetes erecta* named KI4537 that has elevated xanthophyll levels, fertile male flowers, excellent vigor and overall agronomic robustness. KI453 is unique marigold inbred line carrying a mutation in the carotenoid pathway which results in a lutein content >40 mg/g on a dry weight basis in flower petal tissue. The mutation is partially dominant and can therefore increase the lutein content of a hybrid by 50% with only one gene dose. If the mutation is introgressed into a compatible female inbred parent, the resulting hybrid is expected to also have a lutein content >40 mg/g relative to commercially available hybrids which typically average 20 mg/g lutein on a dry weight basis.

Plants of the cultivar KI4537 have not been observed under all possible environmental conditions. The phenotype may vary somewhat with variations in environment and culture such as temperature, light intensity, day length, water status, and/or fertilizer rate or type without, however, any variance in genotype.

An object of the present invention is a marigold plant with a high level of lutein for use as an antioxidant in human and animal food, beverages and personal care products.

Another object of the invention is an inbred line of *Tagetes erecta* that is novel, stable, and uniform and has good agronomic characteristics that confers the trait of hyper-accumulation of lutein to its progeny.

DETAILED DESCRIPTION OF THE INVENTION

The term "M" generation as used herein is the seed (and resulting plants) exposed to a mutagenic agent, "$M_2$" is the progeny of self-pollinated $M_1$ plants, "$M_3$" is the progeny of a selected single self-pollinated $M_2$ plant, and so on. The term "progeny" refers to the plants and seeds of all subsequent generations resulting from a selfed plant from the previous generation.

Example 1—Development of KI4537

KI4537 was identified from a chemical-based mutation breeding and research program. Seeds of commercially available open pollinated variety 'Scarletade' were treated with EMS (Sigma Chemicals, St. Louis) at an optimized dose and duration during June 2009. Treated seed designated as the $M_1$ generation was grown in a proprietary greenhouse. The $M_1$ plants were selfed in isolation to produce $M_2$ seed from each $M_1$ plant.

Each $M_2$ seed was grown to produce $M_2$ flowering plants. Flowers from each $M_2$ plant were collected, freeze dried and quantitated for carotenoid levels using HPLC based, industry standard AOAC method. Briefly, 0.5-1 g ground petal samples were extracted and saponified with 30 mL HEAT extraction solvent (hexane, ethanol, acetone, and toluene in volume ratios of 10:6:7:7) and 2 mL 40% methanolic potassium hydroxide (w/v) in a 56° C. water bath set to shake at 120 rpm for 20 minutes. The extract was analyzed in an HPLC with a Waters Sphersorb CN column (50×4.6 mm, 3 μm). An isocratic elution with mobile phase of hexanes (74.6%), methylene chloride (24.9%), methanol (0.4%), n,n-diisopropylethylamine (0.1%) at 1.000 mL/min flow rate was used. The column temperature was maintained at 25° C. and 10 μL of sample was injected to run for 13 minutes per assay. The diode array detector (DAD) was set at 446 nm. A standard method was used for the quantitation of lutein and zeaxanthin.

Figure 1:
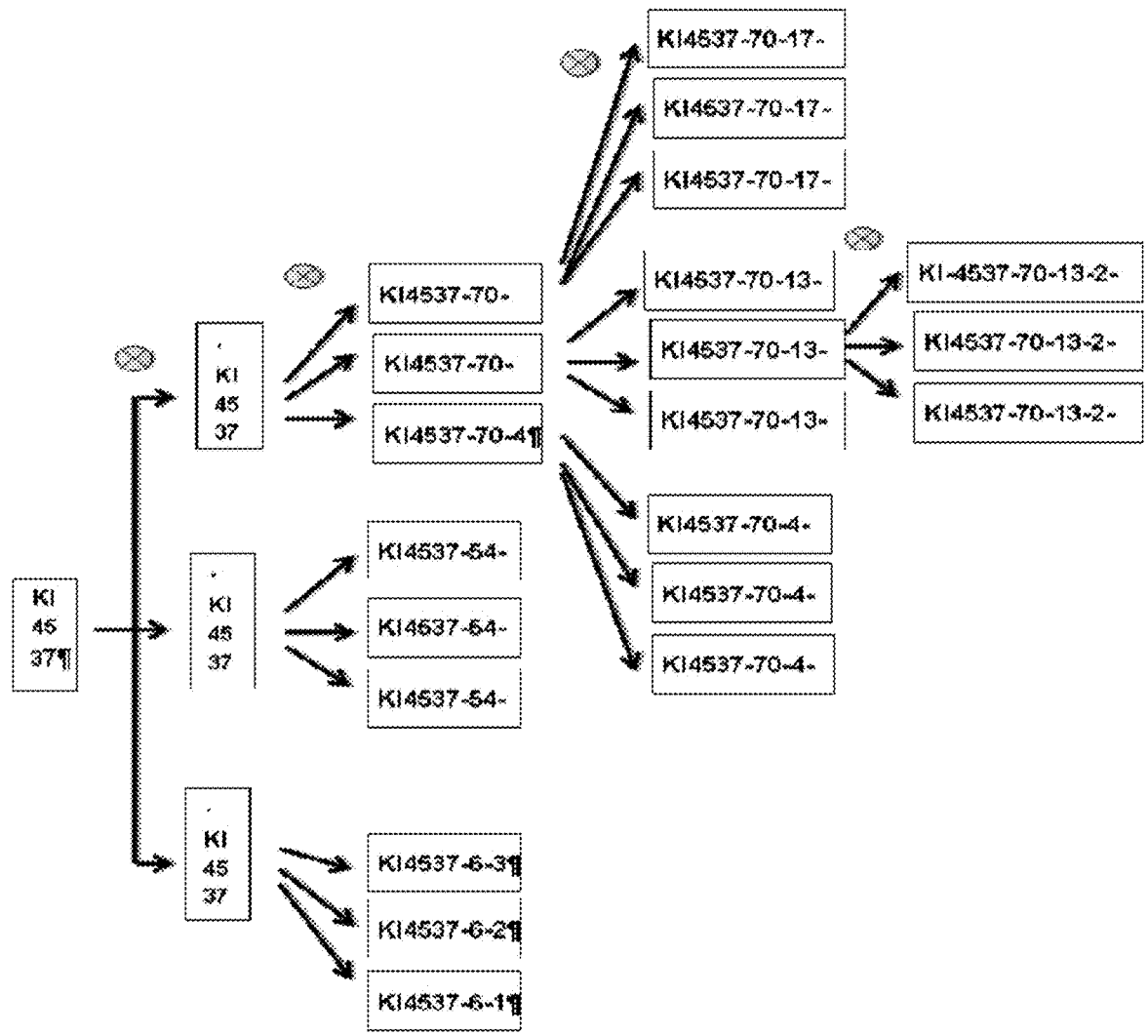
FIG. 1 is a scheme of the development process of male inbred line KI4537.

KI4537 was identified as an M₂ plant with dark orange flowers, exhibiting a noticeable increase in lutein content in comparison to the male line, Scarletade. KI4537 was advanced from $M_2$ to $M_7$ stage using a single-seed descent procedure as shown in FIG. 1. Briefly KI4537 identified as a single $M_2$ plant, was naturally self-pollinated in isolation to produce $M_3$ seed. Eighty $M_3$ plants were generated from $M_3$ seed and flowers were quantitated for lutein and zeaxanthin content using the AOAC method. Based on the carotenoid profile, 2-3 $M_3$ plants with the highest lutein content were selected and naturally self-pollinated in isolation to produce $M_4$ seed. Using the same procedure, KI4537 was advanced from the $M_2$ to the $M_6$ generation producing $M_7$ seed.

Segregation for Lutein in $M_3$ to $M_6$ Generations.

Figure 2:
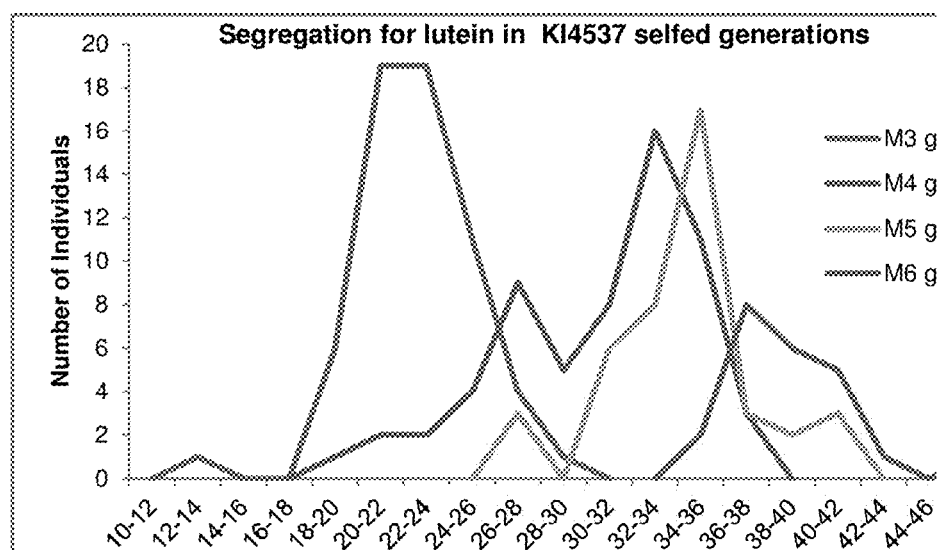
FIG. 2 is a chart of the segregation for lutein content in $M_3$ to $M_6$ generations of KI4537.

The segregation patterns in the $M_3$ to $M_6$ generations of KI4537 are shown in FIG. 2. The mean lutein levels observed in the wild type Scarletade averages 25.5±3.7 mg/g. After five successive generations of single-seed descent breeding (from $M_2$ to $M_6$) in KI4537, followed by carotenoid analysis of flowers in each progeny at each generation, a stable and significant increase in lutein content was observed. Several progeny within each generation of KI4537 were shown to exhibit higher lutein content from the $M_4$ generation onwards (FIG. 2). The frequency and the number of progeny exhibiting higher lutein content increased with each generation of selfing. The mean lutein content increased from 28.6±3.3 mg/g at the $M_2$ generation to 39.4±2.8 mg/g at the $M_6$ generation. Segregation for lutein content was much broader in the $M_3$ (12.7 to 29 mg/g) generation compared to the $M_6$ generation (35-46 mg/g) (Table 1). The segregation pattern of carotenoid profiles in the advanced selfed generations is an indicator of the degree of stability of the trait in an inbred background. At the $M_7$ stage, KI4537 is an inbred line with residual heterozygosity to be theoretically expected to be at ≤1%.

TABLE 1

Lutein content in KI4537 in comparison to Scarletade

|  |  | Average lutein mg/g | Range |
|---|---|---|---|
| M₂ generation | KI4537 | 28.6 |  |
| M₃ generation | KI4537 | 22.5 ± 2.6 | 12.7-29 |
| M₄ generation | KI4537 | 30.6 ± 4.2 | 19.2-38.2 |
| M₅ generation | KI4537 | 34.2 ± 3.3 | 26.1-41.6 |
| M₆ generation | KI4537 | 39.6 ± 2.9 | 34.5-46 |
| Open pollinated | Scarletade | 25.2 ± 3.2 | 17.8-29.9 |

In accordance with one aspect of the present invention, provided is a inbred marigold seed and plants thereof designated KI4537. The present invention further relates to a method for producing inbred marigold seeds that includes, but is not limited to, the steps of planting seed of inbred marigold KI4537 in proximity to itself or to different seed from a same family or line, growing the resulting marigold plants, cross-pollinating the resulting marigold plants, and harvesting resultant seed obtained from such inbred plants using techniques standard in the agricultural arts such as would be necessary to bulk-up seed such as for hybrid production. The present invention also relates to inbred seed produced by such a method.

In any cross between inbred marigold plant KI4537 and another inbred marigold plant, KI4537 may be designated as the male (pollen parent) or the female (seed parent). The present invention also relates to a marigold plant that expresses substantially all of the physiological and morphological characteristics of inbred marigold plant KI4537 and to a substantially homogenous population of marigold plants having all the physiological and morphological characteristics of inbred marigold plant KI4537. Any marigold plants produced from inbred marigold plant KI4537 are contemplated by the present invention and are, therefore, within the scope of this invention. A description of physiological and morphological characteristics of marigold plant KI4537 is presented in Table 2.

It should be appreciated by one having ordinary skill in the art that, for the quantitative characteristics identified in Table 2, the values presented are typical values. These values may vary due to the environment and accordingly, other values that are substantially equivalent are also within the scope of the invention.

Inbred marigold line KI4537 shows uniformity and stability within the limits of environmental influence for the traits described in Table 2. Inbred KI4537 has been self-pollinated a sufficient number of generations with careful attention paid to uniformity of plant type to ensure the homozygosity and phenotypic stability necessary to use in large scale, commercial production. The line has been increased both by hand in isolated fields with continued observations for uniformity. No variant traits have been observed or are expected in KI4537.

The plants of the present invention have the taxonomic description of being genus *Tagetes*, species *erecta*, family Asteraceae and the common name marigold. Table 2 sets out a description of traits of the plants taken from plants growing in a greenhouse in Hereford, Tex., in the summer. Table 2 sets out the characteristic traits of KI4537 and Table 3 sets out the definitions of the traits of Table 2.

TABLE 2

Characteristics of KI4537 at vegetative and flowering stage
Ploidy: Diploid
Chromosome number: 12 sets
Greenhouse Observations

|  | Average | Range |
|---|---|---|
| Growth Form | Upright |  |
| Plant height class (flowering) | Tall |  |
| Flowering Season | Mid-Season |  |
| Flower Type | Chrysanthemum |  |
| Flower Fullness | Semi-double |  |
| Silhouette | Flattened |  |
| Number of Flower heads per plant (98 days) | 22 | 20-25 |
| Flower Head Diameter | 5.2 cm | 4.5-6.0 cm |
| Flower Odor | Mild "Marigold" |  |
| Flower Head Color | Dark Orange |  |
| Days from planting to first flower | 70 days | 65-70 days |
| Length of flowering season | 140 days | 135-145 days |
| Plant height at maturity (Flowering) (98 days) | 102 cm | 96.5-112 cm |
| Plant width class (flowering) | Semi-compact |  |
| Leaf Type | Compound |  |
| Leaf Shape | Lanceolate |  |
| Leaf Margin | Dentate |  |
| Leaf Width | 4.5 cm | 3.8-5.5 cm |
| Leaf Length | 12.0 cm | 10-14 cm |
| Leaf Color | Green |  |
| Petiole Anthocyanin | Mild |  |
| Stem Profile | Straight |  |
| Stem Structure | Intermediate |  |
| Node Length (middle of plant) (flowering) (98 days) | 3.7 cm | 3-4.5 cm |
| Number of internodes below first branch | 1 |  |

TABLE 2-continued

Characteristics of KI4537 at vegetative and flowering stage
Ploidy: Diploid
Chromosome number: 12 sets
Greenhouse Observations

| | Average | Range |
|---|---|---|
| Number of first order branches (flowering) (98 days) | 32.8 | 31-35 |

TABLE 3

Description of Vegetative and Flowering Characteristics.

| | |
|---|---|
| Ploidy | Number of sets of chromosomes |
| Chromosome Number | Number of chromosomes |
| Plant Height (Flowering) | Measure length of the plant from top of soil media to highest plant growth |
| Plant Height Class | Height comparable with other marigold varieties |
| Growth Form | Plant phenotype |
| Leaf Type | Type of leaf |
| Leaf Shape | Structure of leaf |
| Leaf Margin | Structure of leaf edge |
| Leaf width (cm) | Width of leaf structure from fully developed leaf from mid-section of plant |
| Leaf Length (cm) | Length of leaf structure from fully developed leaf from mid-section of plant |
| Leaf Color | Visual color of leaf |
| Petiole Anthocyanin | Red pigmentation of leaf stalk |
| Stem profile | Shape of Stem |
| Stem Structure | Pliability of stem |
| Node length | An internode measured at the mid-section of the main stalk of the plant |
| Number of nodes below first branch | Visual number of internodes below first branch |
| Number of first order branches | Number of branches generating from the main stalk |
| Days from planting to first flower | Observed days between sowing to first open flower |
| Length of flowering season | Observed days between sowing to end of flowering |
| Flowering Season | Designated by number of days to flower compared to other crops |
| Silhouette | Petal Structure |
| Number of Flower heads per plant | Number of flowers or buds per plant |
| Flower head diameter | Diameter of stage 3 flower |
| Flower Odor | Strength of flower fragrance |
| Flower Head Color | Petal color |

In an embodiment, the plant KI4537 produces lutein comprising greater than 26 mg/g dry weight lutein and preferably greater than 40 mg/g dry weight lutein.

The present invention is related to the development of a novel, stable, inbred line of *Tagetes erecta*. This line is unique and clearly distinct from all other existing varieties of *Tagetes erecta*. Line KI4537 has fertile male flowers and is particularly suited for use as a male inbred line which is crossed with female plants to produce hybrid seed that will result in plants having plant tissues, particularly flower petals, that are high in lutein. The mutation present in KI4537 is partially dominant and can therefore increase the lutein content of a hybrid by 50% with only one gene dose. It is expected that if the mutation is introgressed into a compatible female inbred parent, the resulting hybrid will also have a lutein content >40 mg/g relative to commercially available hybrids which typically average 20 mg/g lutein on a dry weight basis.

Various breeding schemes may be used to produce new inbred marigold lines from KI4537. In one method, generally referred to as the pedigree method, KI4537 may be crossed with another different marigold plant such as a second inbred parent marigold plant, which either itself exhibits one or more selected desirable characteristic(s) or imparts selected desirable characteristic(s) to a hybrid combination. Examples of potentially desired characteristics include greater flower yield, higher lutein content, reduced time to crop maturity, better agronomic quality, resistance and/or tolerance to insecticides, herbicides, pests, heat and drought, and disease, and uniformity in germination times, stand establishment, growth rate, maturity and flower size. If the two original parent marigold plants do not provide all the desired characteristics, then other sources can be included in the breeding population. Elite inbred lines, that is, pure breeding, homozygous inbred lines, can also be used as starting materials for breeding or source populations from which to develop inbred lines.

Thereafter, resulting seed is harvested and resulting superior progeny plants are selected and selfed or sib-mated in succeeding generations, such as for about 5 to about 7 or more generations, until a generation is produced that no longer segregates for substantially all factors for which the inbred parents differ, thereby providing a large number of distinct, pure-breeding inbred lines.

In another embodiment for generating new inbred marigold plants, generally referred to as backcrossing, one or more desired traits may be introduced into inbred parent marigold plant KI4537 (the recurrent parent) by crossing the KI4537 plants with another marigold plant (referred to as the donor or non-recurrent parent) which carries the gene(s) encoding the particular trait(s) of interest to produce $F_1$ progeny plants. Both dominant and recessive alleles may be transferred by backcrossing. The donor plant may also be an inbred, but in the broadest sense can be a member of any plant variety or population cross-fertile with the recurrent parent. Next, $F_1$ progeny plants that have the desired trait are selected. Then, the selected progeny plants are crossed with KI4537 to produce backcross progeny plants. Thereafter, backcross progeny plants comprising the desired trait and the physiological and morphological characteristics of marigold inbred line KI4537 are selected. This cycle is repeated for about one to about eight cycles, preferably for about 3 or more times in succession to produce selected higher backcross progeny plants that comprise the desired trait and all of the physiological and morphological characteristics of marigold inbred line KI4537 listed in Table 2 as determined at the 5% significance level when grown in the same environmental conditions. Exemplary desired trait(s) include insect resistance, herbicide resistance, yield stability, yield enhancement and resistance to bacterial, fungal and viral disease. One of ordinary skill in the art of plant breeding would appreciate that a breeder uses various methods to help determine which plants should be selected from the segregating populations and ultimately which inbred lines will be used to develop hybrids for commercialization. In addition to the knowledge of the germplasm and other skills the breeder uses, a part of the selection process is dependent on experimental design coupled with the use of statistical analysis. Experimental design and statistical analysis are used to help determine which plants, which family of plants, and finally which inbred lines and hybrid combinations are significantly better or different for one or more traits of interest. Experimental design methods are used to assess error so that differences between two inbred lines or two hybrid lines can be more accurately determined. Statistical analysis includes the calculation of mean values, determination of the statistical significance of the sources of variation, and the calculation of the appropriate variance components. Either a five or a one percent significance level is customarily used to determine whether a difference that occurs for a given trait is real or due to the environment or experimental error. One of ordinary skill in the art of plant breeding would know how to evaluate the traits of two plant varieties to determine if there is no significant difference between the two traits expressed by those varieties. Mean trait values may be used to determine whether trait differences are significant, and preferably the traits are measured on plants grown under the same environmental conditions.

Of course, the other marigold plant may be the recurrent parent whereby the mutation associated with high lutein values in KI4537 is transferred to the recurrent parent following the foregoing process. It is expected that use of such an inbred line in a cross with KI4537 would result in hybrid marigold plants with greater than 40 mg/g lutein on a dry matter basis.

This method results in the generation of inbred marigold plants with substantially all of the desired morphological and physiological characteristics of the recurrent parent and the particular transferred trait(s) of interest. Because such inbred marigold plants are heterozygous for loci controlling the transferred trait(s) of interest, the last backcross generation would subsequently be selfed to provide pure breeding progeny for the transferred trait(s).

It should be appreciated by those having ordinary skill in the art that backcrossing can be combined with pedigree breeding as where inbred KI4537 is crossed with another marigold plant, the resultant progeny are crossed back to inbred KI4537 and thereafter, the resulting progeny of this single backcross are subsequently inbred to develop new inbred lines. This combination of backcrossing and pedigree breeding is useful for example when recovery of fewer than all of the KI4537 characteristics than would be obtained by a conventional backcross are desired.

Once inbred lines are created, the next step is to determine if the inbreds have any value. This is accomplished by techniques of measuring the combining ability of the new inbred plant, as well as the performance of the line itself. Combining ability refers to a line's contribution as a parent when crossed with other lines to form hybrids. Specific combining ability (SCA) refers to the ability of a line to cross to another specific inbred to form a hybrid. General combining ability (GCA) refers to the ability of a line to cross to a wide range of lines to form hybrids. The methodology of forming hybrids to evaluate an inbred line's contribution as a parent for the purpose of selecting superior lines is interchangeably known as experimental, top or test crossing.

In accordance with processes of the present invention, a hybrid plant having inbred KI4537 as a parent is crossed with itself or any different marigold plant such as an inbred marigold plant or a hybrid marigold plant to develop a novel inbred line. For example, a hybrid marigold plant having inbred marigold plant KI4537 as a parent may be inbred, i.e., crossed to itself or sib-pollinated, and the resulting progeny each selfed for about 5 to about 7 or more generations, thereby providing a set of distinct, pure-breeding inbred lines wherein each of the lines received all of its alleles from the hybrid marigold plant having inbred marigold plant KI4537 as a parent. In other embodiments, a hybrid marigold plant having inbred marigold plant KI4537 as a parent is crossed with a different marigold plant that may include any inbred marigold plant that is not inbred marigold plant KI4537, any hybrid marigold plant that does not have KI4537 as a parent, another germplasm source, a mutation inducing stock, or a trait donor plant, thereby providing a set of distinct, pure-breeding inbred lines. The resulting inbred lines could then be crossed with other inbred or non-inbred lines and the resulting inbred progeny analyzed for beneficial characteristics. In this way, novel inbred lines conferring desirable characteristics could be identified.

In yet another aspect of the invention, processes are provided for producing marigold seeds or plants, which processes generally comprise crossing a first parent marigold plant with a second parent marigold plant wherein at least one of the first parent marigold plant or the second parent marigold plant is inbred parent marigold plant KI4537. In some embodiments of the present invention, the first inbred marigold plant is KI4537 and is a female and in other embodiments the first inbred marigold plant is KI4537 and is a male. These processes may be further exemplified as processes for preparing hybrid marigold seed or plants, wherein a first inbred marigold plant is crossed with a second marigold plant of a different, distinct variety to provide a hybrid that has, as one of its parents, the inbred marigold plant line KI4537. In this case, a second inbred line is selected which confers desirable characteristics when in hybrid combination with the first inbred line. In these processes, crossing will result in the production of seed. The seed production occurs regardless whether the seed is collected.

Any time the inbred marigold plant KI4537 is crossed with another, different marigold inbred, a first generation ($F_1$) marigold hybrid plant is produced. As such, an $F_1$ hybrid marigold plant may be produced by crossing KI4537 with any second inbred marigold plant. Therefore, any $F_1$ hybrid marigold plant or marigold seed which is produced with KI4537 as a parent is part of the present invention.

When inbred marigold plant KI4537 is crossed with another inbred plant to yield a hybrid, the original inbred can serve as either the maternal or paternal plant with basically, the same characteristics in the hybrids. Occasionally, maternally inherited characteristics may express differently depending on the decision of which parent to use as the female. However, often one of the parental plants is preferred as the maternal plant because of increased lutein yield and preferred production characteristics. It is generally preferable to use KI4537 as the male parent.

For a decision to be made to advance a hybrid, it is not necessary that the hybrid be better than all other hybrids. Rather, significant improvements must be shown in at least some traits that would create value for some applications or markets. Some testcross hybrids are eliminated despite being similarly competitive relative to the current commercial hybrids because of the cost to bring a new hybrid to market requires a new product to be a significant improvement over the existing product offering.

All plants produced using inbred marigold plant KI4537 as a parent are within the scope of this invention, including plants derived from inbred marigold plant KI4537. This includes plants essentially derived from inbred KI4537 with the term "essentially derived variety" having the meaning ascribed to such term in 7 U.S.C. §2104(a)(3) of the Plant Variety Protection Act, which definition is hereby incorporated by reference. This also includes progeny plant and parts thereof with at least one ancestor that is inbred marigold plant KI4537 and more specifically where the pedigree of this progeny includes 1, 2, 3, 4, and/or 5 or cross pollinations to inbred marigold plant KI4537, or a plant that has KI4537 as a progenitor. All breeders of ordinary skill in the art maintain pedigree records of their breeding programs. These pedigree records contain a detailed description of the breeding process, including a listing of all parental lines used in the breeding process and information on how such line was used. Thus, a breeder would know if KI4537 were used in the development of a progeny line, and would also know how many breeding crosses to a line other than KI4537 were made in the development of any progeny line. A progeny line so developed may then be used in crosses with other, different, marigold inbreds to produce first generation F1 marigold hybrid seeds and plants with superior characteristics.

Accordingly, another aspect of the present invention is methods for producing an inbred marigold line KI4537-derived marigold plant. This method for producing a KI4537-derived marigold plant, comprises: (a) crossing inbred marigold plant KI4537 with a second marigold plant to yield progeny marigold seed; and, (b) growing the progeny marigold seed, (under plant growth conditions), to yield the KI4537-derived marigold plant. Such methods may further comprise the steps of: (c) crossing the KI4537-derived marigold plant with itself or another marigold plant to yield additional KI4537-derived progeny marigold seed; (b) growing the progeny marigold seed of step (d) (under plant growing conditions), to yield additional KI4537-derived marigold plants; and (e) repeating the crossing and growing steps of (c) and (d) from 0 to 7 times to generate further KI4537-derived marigold plants. Still further, this may comprise utilizing methods of haploid breeding and plant tissue culture methods to derive progeny of the KI4537-derived marigold plant.

With the advent of molecular biological techniques that have allowed the isolation and characterization of genes that encode specific protein products, scientists in the field of plant biology developed a strong interest in engineering the genome of plants to contain and to express foreign genes, or additional, or modified versions of native or endogenous genes (perhaps driven by different promoters) to alter the traits of a plant in a specific manner. Such foreign, additional and/or modified genes are referred to herein collectively as "transgenes." The present invention, in particular embodiments, also relates to transformed versions of the claimed inbred marigold line KI4537 containing one or more transgenes, particularly genes that encode resistance to a herbicide.

Numerous methods for plant transformation have been developed, including biological and physical, plant transformation protocols. See, for example, Miki et al., "Procedures for Introducing Foreign DNA into Plants" in Methods in Plant Molecular Biology and Biotechnology, Glick, B. R. and Thompson, J. E. Eds. (CRC Press, Inc., Boca Raton, 1993) pages 67-88. In addition, expression vectors and in vitro culture methods for plant cell or tissue transformation and regeneration of plants are available. See, for example, Gruber et al., "Vectors for Plant Transformation" in Methods in Plant Molecular Biology and Biotechnology, Glick, B. R. and Thompson, J. E. Eds. (CRC Press, Inc., Boca Raton, 1993) pages 89-119.

The foregoing methods for transformation would typically be used for producing transgenic inbred lines. Transgenic inbred lines could then be crossed, with another (non-transformed or transformed) inbred line, in order to produce a transgenic hybrid marigold plant. Alternatively, a genetic trait which has been engineered into a particular marigold line using the foregoing transformation techniques could be moved into another line using traditional backcrossing techniques that are well known in the plant breeding arts. For example, a backcrossing approach could be used to move an engineered trait from a public, non-elite line into an elite line, or from a hybrid marigold plant containing a foreign gene in its genome into a line or lines which do not contain that gene.

In addition to phenotypic observations, a plant can also be described by its genotype. The genotype of a plant can be described through a genetic marker profile which can identify plants of the same variety, a related variety or be used to determine or to validate a pedigree. Genetic marker profiles can be obtained by techniques such as Restriction Fragment Length Polymorphisms (RFLPs), Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs), Amplified Fragment Length Polymorphisms (AFLPs), Simple Sequence Repeats (SSRs) which are also referred to as Microsatellites, and Single Nucleotide Polymorphisms (SNPs), Isozyme Electrophoresis and Isolelectric Focusing.

Particular markers used for these purposes are not limited to the set of markers disclosed herewithin, but are envisioned to include any type of genetically stable marker and marker profile which provides a means of distinguishing varieties. In addition to being used for identification of inbred parents, a hybrid produced through the use of KI4537 or its parents, and identification or verification of the pedigree of progeny plants produced through the use of KI4537, the genetic marker profile is also useful in breeding and developing backcross conversions.

DEPOSIT INFORMATION

Applicants have made a deposit of at least 2,500 seeds of inbred *Tagetes erecta* line KI4537 with the American Type Culture Collection (ATCC), 10801 University Boulevard, Manassas, Va. 20110 USA, under ATCC Accession No. PTA-121863. The seeds received by the ATCC on Dec. 16, 2014, were taken from a deposit maintained by Kemin Industries, Inc. since prior to the filing date of this application. Access to this deposit will be available during the pendency of the application to the Commissioner of Patents and Trademarks and persons determined by the Commissioner to be entitled thereto upon request. Upon allowance of any claims in the application, the Applicant will make the deposit available to the public pursuant to 37 C.F.R. §1.808. This deposit of the Marigold Inbred Line KI4537 will be maintained in the ATCC depository, which is a public depository, for a period of 30 years, or 5 years after the most recent request, or for the enforceable life of the patent, whichever is longer, and will be replaced if it becomes nonviable during that period. Additionally, Applicant has or will satisfy all of the requirements of 37 C.F.R. §§1.801-1.809, including providing an indication of the viability of the sample upon deposit. Applicant has no authority to waive any restrictions imposed by law on the transfer of biological material or its transportation in commerce.

The foregoing description and drawings comprise illustrative embodiments of the present inventions. The foregoing embodiments and the methods described herein may vary based on the ability, experience, and preference of those skilled in the art. Merely listing the steps of the method in a certain order does not constitute any limitation on the order of the steps of the method. The foregoing description and drawings merely explain and illustrate the invention, and the invention is not limited thereto, except insofar as the claims are so limited. Those skilled in the art that have the disclosure before them will be able to make modifications and variations therein without departing from the scope of the invention.

We claim:

1. A seed of marigold inbred line designated KI4537, or a part of the seed, representative seed of the line having been deposited under ATCC Accession No. PTA-121863.

2. A substantially homogenous population of seeds comprising at least one of the marigold seed of claim 1.

3. A method for producing marigold seed, said method comprising the steps of:
   (a) planting the seed of claim 1 in proximity to another seed of inbred line KI4537 or to a seed of a different line;
   (b) growing plants from the seed;
   (c) cross-pollinating said plants; and,
   (d) harvesting the resultant seed.

4. A marigold seed produced by the method of claim 3.

5. A marigold plant produced by growing the seed of claim 1.

6. A part of the marigold plant of claim 5, selected from the group consisting of an intact plant cell, a plant protoplast, an embryo, pollen, an ovule, a seed, a flower, a petal and a leaf.

7. Pollen of the plant of claim 5.

8. An ovule of the plant of claim 5.

9. A marigold plant, or a part of the marigold plant, having all the physiological and morphological characteristics of the marigold plant, or a part of the marigold plant, of claim 5.

10. A substantially homogenous population comprising at least one of the marigold plant of claim 5.

11. A method for producing a marigold plant, said method comprising the step of:
    (a) crossing inbred marigold plant KI4537, representative seed of the line having been deposited under ATCC Accession No. PTA-121863, with another different marigold plant to yield progeny marigold seed.

12. The method of claim 11, wherein the other, different marigold plant is an inbred marigold plant.

13. The method of claim 11, further comprising the steps of:
    (b) growing the progeny marigold seed from step (a);
    (c) under self-pollinating or sib-pollinating conditions for 5 to 7 generations; and
    (d) harvesting resultant seed.

14. The method of claim 11, further comprising the step of selecting plants obtained from growing at least one generation of the progeny marigold seed for a desirable trait.

15. A method of introducing a desired trait from marigold inbred line KI4537, representative seed of the line having been deposited under ATCC Accession No. PTA-121863, said method comprising the steps of:
    (a) crossing KI4537 plants with plants of another marigold line that comprise a desired trait to produce F1 progeny plants;
    (b) selecting F1 progeny plants that have the desired trait;
    (c) crossing selected progeny plants with said other marigold line plants to produce backcross progeny plants;
    (d) selecting for backcross progeny plants that comprise the desired trait and physiological and morphological characteristics of marigold inbred line KI4537; and
    (e) performing steps (c) and (d) one or more times in succession to produce the selected or higher backcross progeny plants that comprise the desired trait and all of the physiological and morphological characteristics of said other marigold inbred line as determined at the 5% significance level when grown in the same environmental conditions.

16. A method for producing a hybrid marigold seed comprising crossing a first inbred parent marigold plant with a second inbred parent marigold plant and harvesting resultant hybrid marigold seed, wherein the first inbred marigold plant or the second inbred marigold plant is the marigold plant of claim 5.

17. A method for producing a hybrid marigold seed, the method comprising:
    (a) planting in pollinating proximity a seed of the inbred marigold plant of claim 5 and a seed of a second, different inbred marigold plant;
    (b) cultivating the seeds into plants that bear flowers;
    (c) cross pollinating at least some of the cultivated plants; and
    (d) harvesting seeds produced from at least one of the first or second inbred marigold plants.

18. The method according to claim 17, wherein the KI4537 marigold plant is the male parent.

19. The method according to claim 17, wherein the KI4537 marigold plant is the female parent.

20. A hybrid marigold seed produced by the method according to claim 17.

21. A hybrid marigold plant, or parts thereof, produced by growing the hybrid marigold seed of claim 20.

* * * * *